United States Patent [19]
Mukerji et al.

[11] Patent Number: 5,506,209
[45] Date of Patent: Apr. 9, 1996

[54] PRODUCT FOR INHIBITION OF INFECTION OF MAMMALIAN CELLS BY RESPIRATORY SYNCYTIAL VIRUS

[75] Inventors: Pradip Mukerji; Amanda E. Seo, both of Gahanna; Steven N. Anderson, Pickerington; Joseph P. Schaller, Columbus, all of Ohio

[73] Assignee: Abbott Laboratories, Abbott Park, Ill.

[21] Appl. No.: 249,554

[22] Filed: May 26, 1994

[51] Int. Cl.$^6$ .......................... A61K 38/00; A61K 35/20; C07K 1/00
[52] U.S. Cl. .............................. 514/21; 514/12; 530/324; 530/350; 530/360; 530/365; 530/832; 424/535
[58] Field of Search ..................... 514/21, 12; 530/324, 530/350, 360, 365, 832; 424/535

[56] References Cited

FOREIGN PATENT DOCUMENTS

| 0291265 | 11/1988 | European Pat. Off. . |
|---|---|---|
| WO9106308 | 5/1991 | WIPO . |
| WO91/08675 | 6/1991 | WIPO . |
| 93/04171 | 3/1993 | WIPO . |
| WO93/04172 | 3/1993 | WIPO . |
| 94/06306 | 3/1994 | WIPO . |

OTHER PUBLICATIONS

Svanborg et al., Adv. Exp. Med. Biol., 310:167–171 (1991).
Tyrell, "Breast Feeding and Virus Infection", The Immunology of Infant Feeding, ed. A. W. Wikinson, Plenum Press, pp. 55–62 (1981).
Anderson et al., "Microneutralization Test for Respiratory Syncytial Virus Based on an Enzyme Immunoassay", Journal of Clinical Microbiology, 22:1050–1052 (1985).
Laegreid et al, Acta Pediatrica Scandanvica, vol. 75, pp. 696–701, 1986.
"Respiratory Syncytial Virus or Influenza in Adults", Pediatric Notes, 18(4):1 (1994).
Anianson et al., "Anti–adhesive Activity of Human Casein Against Streptococcus pneumoniae and Haemophilus influenzae", Microbial Pathogenesis, 8:315–323 (1990).
Hannson et al., "Expression of Human Milk B–Casein in *Escheria coli*: Comparison of Recombinant Protein with Native Isoforms", Protein Expression and Purification, 4:373–381 (1993).
Lönnerdal et al., "Cloning and Sequencing of a cDNA Encoding Human B–Casein", Federation of European Biochemical Society Letters, 269(1):153–156 (1990).
Okamoto et al., "Antiviral Factors in Human Milk: Implications in Respiratory Syncitial Virus Infection", Acta Paediatrica Scandinavica Supplement, 351:137–143 (1989).
Laegrid et al., "Neutralizing Activity in Human Milk Fractions Against Respiratory Syncytial Virus", Acta Paediatirica Scandanavica, 75:696–701 (1986).

Primary Examiner—Christina Y. Chan
Assistant Examiner—Abdel A. Mohamed
Attorney, Agent, or Firm—Lonnie R. Drayer

[57] ABSTRACT

The infection of mammalian cells by RSV may be inhibited by native human β-casein, a recombinant form of human β-casein, and hydrolysates of both. The human β-casein or hydrolysate may be contained in a liquid enteral nutritional product such as an infant formula. The enteral nutritional product may be used, for example, in the prevention and treatment of respiratory tract infection in infants. The human β-casein or hydrolysate may also be administered as a throat spray or nasally using drops or a spray.

6 Claims, No Drawings

PRODUCT FOR INHIBITION OF INFECTION OF MAMMALIAN CELLS BY RESPIRATORY SYNCYTIAL VIRUS

The present invention relates generally to inhibiting the infection of mammalian cells by Respiratory Syncytial Virus and more specifically to the use of native or recombinant human β-casein and hydrolysates thereof for inhibiting the infection of mammalian cells by Respiratory Syncytial Virus.

Respiratory Syncytial Virus (RSV) is the single most frequent cause of acute respiratory tract infection in infants and children. Infants less than six months of age are most frequently and seriously affected. In most immunologically normal subjects, infection with RSV is limited to the respiratory mucosa, and is associated with the development of bronchiolitis, pneumonia and reactive airway disease. RSV infection in immunocompromised subjects has until recently been associated with increased mortality in infants and increased morbidity in other age groups. It has recently been reported in *PEDIATRIC NOTES*, Vol. 18, No. 9, Jan. 27, 1994, that periods of high incidence of acute respiratory disease and numbers of deaths in elderly people were followed within 2–3 weeks by reports of high numbers of RSV or influenza virus isolates. The analyses indicate that RSV is as important as influenza viruses in causing morbidity and deaths among the elderly.

It has been reported that some respiratory disease may be prevented by breast feeding, and that "bronchiolitis of infants due to respiratory syncytial virus is less frequent in breast fed than in artificially fed infants". While human breast milk can contain antibodies to RSV, it has been found that milk also has antiviral activity that is not due to antibodies. It has been theorized that this effect "may be produced by certain polysaccharides which are found on a number of different molecular constituents of milk." Tyrrell, "BREAST FEEDING AND VIRUS INFECTIONS", *THE IMMUNOLOGY OF INFANT FEEDING*, edited by A. W. Wilkinson, Plenum Press, New York, N.Y. pages 55–62 (1981).

Okamato, et al., "Antiviral Factors in Human Milk: Implications in Respiratory Syncytial Virus Infection", *ACTA PAEDIATRICA SCANDANAVICA SUPPLEMENT*, 351:137–143 (1989) disclose that while the mechanisms of protective immunity to RSV had not been clearly defined, immunity acquired transplacentally or via breast feeding has been suggested to reduce the risk of lower respiratory tract disease. However, this publication focuses upon the role of antibodies transmitted in breast milk or the possible role of breast milk in modulating an infant's RSV immune response.

Laegreid et al., "Neutralizing Activity in Human Milk Fractions against Respiratory Syncytial Virus", *ACTA PAEDIATRICA SCANDANAVICA*, 75:696–701 (1986) reports a study which confirms that human milk may contain RSV-neutralizing activity of a non-immunoglobulin nature as well as RSV-specific antibody. However, the identity and mechanism of the non-immunoglobulin anti-RSV component of human milk is not identified. It is important though to note that Laegreid et al. disclose that RSV-neutralizing components from breast milk may reach an infant's respiratory tract directly as a result of regurgitation and inhalation of milk during and after feeding. The mucosa of the respiratory tract may gain direct protection in this way.

WO 91/06308 filed by Andersson et al. for "ANTIBACTERIAL COMPOSITION", and a published article by the same authors (Aniansson et al., "Anti-adhesive activity of human casein against Streptococcus pneumonia and Haemophilus influenzae", *MICROBIAL PATHOGENESIS*, 8:315–323 (1990) disclose the use of a milk fraction having a molecular weight of at least 5,000 daltons for "therapeutic prophylactic, and/or diagnostic use in infections caused by *S. pneumonae* and/or *H. influenzae*", but it is suggested in these publications that the beneficial effect is provided by kappa-casein. However, the present invention relates to the use of native or recombinant human β-casein and hydrolysates of both to inhibit RSV infections.

WO93/04172 relates to a DNA sequence encoding human β-casein, but does not disclose the capacity of either native or recombinant human β-casein to inhibit the attachment of RSV to human cells.

WO91/08675 discloses an infant formula which contains recombinant forms of both human alpha-lactalbumin and human β-casein. However, this publication discloses only that these human milk proteins will "give a simulated human mother's milk formula that does not exhibit the allergenic properties associated with formulas based on cow or other foreign protein." (page 3, lines 20–22). The use of human β-casein to inhibit the attachment of RSV to human cells is not taught or suggested in said publication.

The two assays (a HEp-2 cell assay and a LLC-MK2 cell assay) which were used for determining the bioactivity of β-casein are described below. These assays have not been published heretofore, although the HEp-2 cell assay was based upon established methodology.

MATERIALS USED IN BOTH ASSAYS

Native Human β-Casein

β-casein isolated from human milk was purchased from Symbicom AB, P. O. Box 1451 S-901 24 Umea Sweden.

Recombinant Human β-Casein

Applicants obtained β-casein cDNA and the expression system from Symbicom AB, P. O. Box 1451, S-901 24 Umea, Sweden. The human β-casein cDNA used had been previously cloned and sequenced by Lonnerdal et al., Cloning and sequencing of a cDNA encoding human milk β-casein. (SEQ.ID NO: 1:) *Federation of European Biochemical Societies Letters* 269, 153–156 (1990). The recombinant human β-casein was obtained from *E. coli* and purified according to the method of Hansson et al., Expression of Human Milk β-Casein in *Escherichia coli*: Comparison of Recombinant Protein with Native Isoforms. *Protein Expression and Purification* 4, 373–381 (1993). To express human β-casein in *E. coli*, β-casein cDNA was cloned under control of a T7 promoter in two different expression vectors. One vector, pS26, was designed for intracellular expression. The other vector, pS28, has a signal sequence for extracellular expression. The procedure followed was substantially that described by Hansson et al.

Human β-casein cDNA was isolated by Hansson et al. as a 1.1-kb EcoRI fragment from a human lambda gt mammary gland library, and was subcloned into pUC19, which was designated pS21. The cDNA was modified by introduction of synthetic oligonucleotides in the 5' and 3' termini. To introduce a suitable cloning site in the 5' end, NdeI, a translational start, was inserted in front of the sequence encoding mature human β-casein. To adapt the initial part of the translated sequence to *E. coli* codon usage, six synthetic oligonucleotides were constructed and ligated. Also, PstI and EcoRI sites were inserted in front of the NdeI site. The sequence of the synthetic fragment was 5'-CTGCAGAAT-TCAT<u>ATGCGTGAAACCATCGAA</u>
<u>TCCCTGAGCTCGAGCGAAGAAT</u>
<u>CGATCACCGAATAC</u>

AAAAAAGTTGAAAAAGTTAAACACGAGGACCAG GATCC- 3'. (SEQ ID NO: 2:) The protein encoding sequence is underlined. The synthetic fragment was cloned into PstI/BamHI-digested pUC19 resulting in plasmid pS24. To insert the rest of the β-casein encoding sequence, a 303-bp AccI/BglII fragment was isolated and cloned into a pUC18 derivative and designated plasmid pS22. Four synthetic oligonucleotides containing the sequence encoding the carboxy-terminal end and translation stop followed by BamHI and EcoRI sites were constructed resulting in the sequence 5'AGATCTACCCTGTGA CTCAGCCACTTGCCCCAGTTCATAACCCCATTAGT GTCTAATAAGGATCCGAATTC-3', (SEQ ID NO: 3:) where the protein encoding sequence is underlined. The synthetic fragment was cloned into BglII/EcoRI digested pS22, resulting in plasmid pS23. To obtain the recombinant modified β-casein encoding fragment, three fragments were ligated: an 89-bp PstI/AvaII fragment from pS24; a 197-bp AvaII/AccI fragment from pS21; and PstI/AccI digested pS23. The resulting plasmid pS25 was digested with NdeI/BamHI and a 641-bp fragment was isolated and cloned into the vector pET-3a. The resulting expression vector was designated pS26.

In order to construct a vector mediating extracellular expression, the E. coli signal sequence of the enterotoxin STII gene was introduced in front of the β-casein encoding sequence. A modified STII sequence with NcoI- and NdeI-compatible ends and an internal ClaI site was obtained by using a synthetic oligonucleotide, 5' -CATGAAAAA-GAATATCGCATTTCTTCTTGCATCGAT GTTCGTTT TTTCTATTGCTACAAATGCATATG-3' (SEQ ID NO: 4:). To insert the signal sequence in front of the β-casein encoding sequence, pS25 was digested with AvaI/EcoRI and a 619-bp fragment was isolated. This fragment was ligated with a synthetic oligonucleotide fragment, 5'CATATG-CACGTGAAACCATCGAATCCCTGAGCTC GAG-3' (SEQ ID NO: 5:), and NdeI/EcoRI-digested pUC19. The resulting plasmid was designated pS27. The final expression vector,pS28, was constructed by ligating three fragments: a 700bp NdeI/HindIII β-casein fragment isolated from pS27, the STII signal sequence, and a NcoI/HindIII-digested pACAT7 vector.

The expression vectors pS26 and pS28 were used to transform E. coli strains BL21(DE3), BL21(DE3)pLysS, and BL21(DE3)pLysE. The bacteria were grown in Luria Broth medium containing 50 µg/ml carbenicillin, and when Bl21(DE3)pLysS and BL21 (DE3)pLysE were used the medium was supplemented with 25 µg/ml chloramphenicol.

For induction of expression the cultures were grown to a density yielding an optical density (OD) of 0.6 at a wavelength of 600 nanometers ($OD_{600}$), then 0.4 mM IPTG was added to induce the T7 system. The cells were harvested about 90 minutes after induction.

Recombinant β-casein was isolated using standard procedures. The inducible T7-based expression system resulted in high-level expression of recombinant β-casein. Bacteria were harvested and the cells pelletted by centrifugation. The supernatant contained the periplasmic proteins and the pellet the cytoplasmic fraction. The recombinant proteins obtained were compared with native β-casein, which had been purified by standard methods including either ion-exchange chromatography followed by reversed-phase HPLC or gel filtration. Recombinant and native β-casein were compared by standard biochemical techniques comprising SDS-PAGE, Western blotting, amino acid analysis, peptide mapping, phosphate analysis, and mass spectrometry. Recombinant β-casein expressed in E. coli was found to comigrate with full-length, nonphosphorylated native human β-casein, which is one of seven native isoforms.

Recombinant human β-casein has also been expressed in S. cerevisiae using the pYES 2.0 vector (Invitrogen Corp., San Diego, Calif.), but the expression level was approximately 10% of that obtained in E. coli. However, Hansson et al. found that S. cerevisiae appeared to express phosphorylated human milk β-casein.

β-Casein Hydrolysates

The human β-casein (both native and recombinant) was digested using the specific endoproteinase GLU-C (Sigma, sequencing grade) which catalyzes the hydrolysis of peptide bonds at the C-terminal of glutamic acid residue. After monitoring the digest using high pressure liquid chromatography, an enzyme to protein ratio of 1:100 (weight/weight) was chosen for a 30 hour digestion at 37° C. in 0.1M $NH_4HCO_3$, pH 7.8. These digests were dried and resuspended in appropriate buffers prior to use in the assays discussed above.

INHIBITION OF HUMAN RSV INFECTION OF HEp-2 CELLS

The Long strain of RSV was grown in HEp-2 cells under Eagle minimal essential medium (MEM) with 2% fetal bovine serum (FBS). The virus was harvested at a cytopathic effect (CPE) of 3 to 4+, sonicated for 10 seconds at 50% power with a Microson ultrasonic bell disrupter (Heat Systems - Ultrasonics, Inc., Farmingdale, N.Y.), divided into portions and stored at –70° C. The same preparation of virus was used for a series of tests, but a fresh sample was used for each test run.

The neutralization tests were performed in 96-well, flat-bottomed, tissue culture, microtiter plates (catalog no. 3596; Costar, Cambridge, Mass.). Serum or a monoclonal antibody (MAb) in the form of ascites fluid, which had been heat inactivated at 56° C. for 30 min., was added to duplicate wells and serial fourfold dilutions were performed in the microtiter plates. All dilutions were in MEM-2% FBS, and the final volume was 75 µl per well. Approximately 60 50% tissue culture infective doses of virus in 25 µl of MEM-2% FBS then were added to each well, and the mixture was incubated for 2 h at 4° C.

Approximately 15,000 HEp-2 cells in 100 µl of MEM-5% FBS were added to each well, and the plates were wrapped in cellophane and incubated at 35.5° C. in a humidified $CO_2$ incubator for 3 days. The plates were fixed by aspirating the contents of the wells, washing three times with phosphate-buffered saline (PBS) at pH 7.2 with 0.5% Tween 20, adding 75 µl of an 80% (vol/vol) solution of acetone-PBS, and incubating for 15 min at 4° C. After the incubation period, the contents were aspirated, and the plates were air dried.

The Enzyme Linked Immuno Sorbent Assay (ELISA) was performed on the same day as the fixation, or the plates were stored overnight at 4° C. and the ELISA was performed on the next day. For the ELISA, the wells were precoated with 200 µl of PBS with 0.5% gelatin for 30 min at 35° C., the contents were aspirated, the wells were washed with PBS (pH 7.2)-0.5% Tween 20 and 75 µl of bovine anti-RSV serum (BaRSV) Burroughs Wellcome Co., Research Triangle Park, N.C.) diluted in PBS 0.5% gelatin plus 0.5% Tween 20 and 2% normal goat serum was added and incubated for 1 hour at 35.5° C. The contents were aspirated, the wells were washed, and 75 µl of peroxidase-conjugated, goat anti-bovine immunoglobulin G (IgG) (Kirkegaard and Perry Laboratories, Inc., Gaithersburg, Md.) diluted in PBS- 0.5% gelatin-0.5% Tween 20-2% normal goat serum was added and incubated for 1 hour at 35.0° C. The contents of the wells were aspirated again, the wells were washed, and 125 μl of substrate (0.4 mg of o-phenylenediamine dihydrochloride per ml 0.015% $H_2O_2$) in 0.15M citrate phosphate buffer (pH 5.5) was added and incubated at room temperature for 40 to 45 min. The reaction was stopped with 3.5M HCl, and the $A_{490}$ was read with a microplate reader. Each dilution of antibody was run in duplicate, and each plate included control wells with uninfected cells, a back titration, i.e. titration of the virus inoculum in MEM-2% FBS, and a titration of a preimmune or nonneutralizing antibody. An absorbance reading of greater than or equal to 3 standard deviations above the mean of 15 control wells was considered to be evidence of virus replication. The dilutions of BaRSV (1:1,000) and goat anti-bovine IgG (1:5,000) used through the study initially was determined by checkerboard titrations.

This assay was based upon the disclosure of Anderson et al., "Microneutralization Test for Respiratory Syncytial Virus Based on an Enzyme Immunoassay", *JOURNAL OF CLINICAL MICROBIOLOGY*, December 1985, pages 1050–1052.

RESULTS FROM HEp-2 CELL ASSAY

The human and bovine β-casein solutions were prepared first in 20 mM ethanolamine, 6M urea, pH 9.5 and then washed twice in PBS by ultrafiltration using Centricon membrane filters (Amicon, Mass.) with a cut-off of 3,000 daltons. After resuspending in appropriate buffer for the HEp-2 cell assay described above, these samples were tested in the assay. Experiments with different designated numbers were performed in different days. As shown in Table 1, human β-casein caused an inhibition of infection/virus replication of 50% or more at concentrations of 0.4 mg/ml or greater. It should be noted than when referring to Table 1, a higher percent inhibition indicates a higher level of bioactivity of the "AGENT", and a lower percent inhibition indicates a lower level of activity of the "AGENT". Bovine β-casein was not significantly active even at 1.6 mg/ml. These results indicated that β-casein from human milk has different bioactivity compared to the bovine milk β-casein.

TABLE 1

INHIBITION OF HUMAN RSV INFECTION OF HEp-2 CELLS

| AGENT USED | CONC. (mg/ml) | PERCENT INHIBITION |
|---|---|---|
| β-Casein Isolated from Human Milk | 1.6 | >90 |
|  | 0.8 | >90 |
|  | 0.4 | >90 |
| Bovine β-casein | 1.6 | 0 |
|  | 0.8 | 0 |
|  | 0.4 | 0 |

Data shown are average of three replicates.

INHIBITION OF HUMAN RSV INFECTION OF LLC-MK2 CELLS

The RSV inhibition assay quantitatively determines the ability of a test reagent (antibody or other bioactive compound) to inhibit the infection of monkey kidney cells (LLC-MK2) (ATCC CCL 7) in microtiter plates. Infected cells were identified using an immunoperoxidase method. The method is described briefly below.

LLC-MK2 cells were seeded into fibronectin treated Costar microtiter plates ($5.0 \times 10^3$ cells per well) and incubated for 3–4 days prior to use in the infectivity reduction assay. On the day of assay, the Long strain of RSV was diluted in MEM to 10–20,000 infected cell units (ICU/mL), and added to an equal volume (200 μL) of serially diluted sample preparations at suitable concentration (ex. 0.5, 1.0, and 2.0 mg casein/mL). Mixtures of diluted test samples and virus were then incubated for 2 hours at 4° C. prior to adding to LLC-MK2 cells. Prior to addition of the diluted sample-virus mixtures to microtiter plates, culture medium was removed and the monolayers rinsed one time with MEM. All diluted sample-virus mixtures were tested in triplicate wells. The diluted sample-virus mixtures were allowed to absorb to LLC-MK2 monolayers for 2 hours at 37° C. in a humidified $CO_2$ incubator. Following incubation, 150 μl of MEM was added to all wells and the plates incubated at 37° C. for 16 hours in the $CO_2$ incubator. After overnight incubation, the culture medium was removed and the monolayers fixed with cold ethanol. After fixing, microtiter plates were rinsed once with 200 μl Dulbecco's PBS per well, and bovine anti-RSV antibody (200 μl) was added to all wells. Following a 30 minute incubation at room temperature and three rinses with PBS/0.5% chick albumen (PBS/CEA), peroxidase labeled rabbit anti-bovine IgG was added to all wells and incubated at room temperature for 30 minutes. Microtiter plates were then rinsed 3 times with PBS/CEA and diaminobenzadine substrate added and incubated for 20 minutes. Plates were then rinsed as above with PBS/CEA, and the number of stained RSV-infected cells per well determined using an inverted microscope.

RESULTS FROM LLC-MK2 CELL ASSAY

The proteins described in Table 1 were also tested in this assay for activity. Once again, native human milk β-casein was found to be active at concentrations of 1 mg/ml or greater while bovine β-casein was not significantly active. The GLU-C hydrolysates of both native and recombinant human β-casein were active at concentrations of 0.75 mg/ml and higher. Hence these results indicated that the recombinant human β-casein, native human β-casein and their hydrolysates inhibit RSV infection of both HEp-2 mammalian cells and LLC-MK2 mammalian cells.

TABLE 2

INHIBITION OF HUMAN RSV INFECTION OF LLC-MK2 CELLS

| AGENT USED | CONC. (mg/ml) | PERCENT INHIBITION |
|---|---|---|
| β-Casein Isolated from Human Milk | 1.5 | 87 |
|  | 1 | 69 |
|  | 0.75 | 33 |
|  | 0.38 | 20 |
| Bovine β-casein | 1 | 21 |
|  | 0.5 | 23 |
|  | 0.25 | 6 |
| Hydrolysate of β-casein Isolated from Human Milk | 1.5 | 99 |
|  | 0.75 | 77 |
|  | 0.38 | 60 |
| Hydrolysate of Recombinant Human β-Casein | 1.5 | 84 |
|  | 0.75 | 42 |
|  | 0.38 | 25 |
| GLU-C Enzyme Control | .025 | 64 |

TABLE 2-continued

INHIBITION OF HUMAN RSV INFECTION
OF LLC-MK2 CELLS

| AGENT USED | CONC. (mg/ml) | PERCENT INHIBITION |
|---|---|---|
| | .0125 | 27 |
| | .0068 | 19 |

Data shown are average of four replicates.

It has been concluded from the foregoing experiments that β-casein isolated from hum:an milk, a recombinant form of the β-casein contained in human milk, and hydrolysates of both, inhibits the infection of mammalian cells by RSV. Furthermore, inasmuch as RSV has been identified in the literature as being associated with respiratory tract infection, it has been concluded that the above identified forms of human β-casein may be employed in the prevention: and treatment of respiratory tract infection in humans, especially in human infants. In view of the therapeutic effect of enterally ingested human milk containing human β-casein upon respiratory tract infection, it is concluded that the above identified forms of human β-casein have a therapeutic benefit when enterally (orally) ingested.

The therapeutic effects described in the preceding paragraph may be provided by an enteral liquid nutritional product, such as infant formula, comprising one or more proteins not contained in human milk in combination with a therapeutically effective amount of at least one of the forms of human β-casein described in the preceding paragraph. It is further concluded that the infection of mammalian cells by RSV may be inhibited by administering via a nasal passageway, or as a throat spray, a formulation containing a therapeutically effective amount of at least one of the forms of human β-casein identified in the preceding paragraph. Such a nasally administered formulation may be in the form of either drops or a spray.

The enteral nutritional, throat spray and nasal products and methods are believed to be effective in inhibiting the infection of mammalian cells by RSV because the interaction of the human β-casein and RSV is believed to occur via direct contact rather than following digestion and absorption of the β-casein.

It is believed that the above identified forms of human β-casein may be incorporated into any standard or specialized enteral liquid nutritional product containing at least one protein not found in human milk, such as bovine milk based or soy based infant formulas, and other beverages consumed by young children. In a preferred embodiment no proteins or hydrolysates thereof found in human milk, other than β-casein, are contained in the liquid enteral nutritional product. Such a product has utility in the treatment and prevention of respiratory tract infection in human infants.

While preferred embodiments of the invention have been disclosed, it will be apparent to those skilled in the art that various changes and modifications may be made therein without deviating from the spirit or scope of this invention.

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
        ( A ) LENGTH:1065 base pairs
        ( B ) TYPE:Nucleic acid
        ( C ) STRANDEDNESS: Single
        ( D ) TOPOLOGY: Unknown ( i i ) MOLECULE TYPE: Cloned cDNA representing the product of a human
            genomic DNA segment.
        ( A ) DESCRIPTION: Human milk beta- casein ( i i i ) HYPOTHETICAL:

( i v ) ANTI-SENSE:

( v ) FRAGMENT TYPE:

( v i ) ORIGINAL SOURCE: Human
        ( A ) ORGANISM: Homo sapiens
        ( B ) STRAIN:
        ( C ) INDIVIDUAL ISOLATE:
        ( D ) DEVELOPMENTAL STAGE: Adult
        ( E ) HAPLOTYPE:
        ( F ) TISSUE TYPE: Mammary Gland
        ( G ) CELL TYPE:
        ( H ) CELL LINE:
        ( I ) ORGANELLE:

( v i i ) IMMEDIATE SOURCE: Human Mammary Gland
        ( A ) LIBRARY:
        ( B ) CLONE:

( v i i i ) POSITION IN GENOME:

(A) CHROMOSOME/SEGMENT:
(B) MAP POSITION:
(C) UNITS:

(ix) FEATURE:
(A) NAME/KEY:
(B) LOCATION:
(C) IDENTIFICATION METHOD: DNA sequencing and restriction analysis
(D) OTHER INFORMATION: The encoded product of nucleotide SEQ ID NO: 1: is the human milk protein, β-casein.

(x) PUBLICATION INFORMATION:
(A) AUTHORS: B. Lonnerdal et al
(B) TITLE: Cloning and Sequencing of a cDNA encoding human milk beta- casein.
(C) JOURNAL:Federation European Biochemical Society Letters
(D) VOLUME:269
(E) ISSUE:
(F) PAGES:153–156
(G) DATE:1990
(H) DOCUMENT NUMBER:
(I) FILING DATE:
(J) PUBLICATION DATE:
(K) RELEVANT RESIDUES:

(xi) SEQUENCE DESCRIPTION: SEQ ID NO: 1:

| | | | | | | | | | | | | | | |
|---|---|---|---|---|---|---|---|---|---|---|---|---|---|---|
| CGG | ATG | AAG | GTC | CTC | ATC | CTC | GCC | TGC | CTG | GTG | GCT | CTT | GCT | CTT | 45 |
| GCA | AGG | GAG | ACC | ATA | GAA | AGC | CTT | TCA | AGC | AGT | GAG | GAA | TCT | ATT | 90 |
| ACA | GAA | TAC | AAG | AAA | GTT | GAG | AAG | GTT | AAA | CAT | GAG | GAC | CAG | CAG | 135 |
| CAA | GGA | GAG | GAT | GAA | CAC | CAG | GAT | AAA | ATC | TAC | CCC | TCT | TTC | CAG | 180 |
| CCA | CAG | CCT | CTG | ATC | TAT | CCA | TTC | GTT | GAA | CCT | ATC | CCC | TAT | GGT | 225 |
| TTT | CTT | CCA | CAA | AAC | ATT | CTG | CCT | CTT | GCT | CAG | CCT | GCT | GTG | GTG | 270 |
| CTG | CCT | GTC | CCT | CAG | CCT | GAA | ATA | ATG | GAA | GTC | CCT | AAA | GCT | AAA | 315 |
| GAC | ACT | GTC | TAC | ACT | AAG | GGC | AGA | GTG | ATG | CCT | GTC | CTT | AAA | TCT | 360 |
| CCA | ACG | ATA | CCC | TTT | TTT | GAC | CCT | CAA | ATC | CCA | AAA | CTC | ACT | GAT | 405 |
| CTT | GAA | AAT | CTG | CAT | CTT | CCT | CTG | CCT | CTG | CTC | CAG | CCC | TTG | ATG | 450 |
| CAG | CAG | GTC | CCT | CAG | CCT | ATT | CCT | CAG | ACT | CTT | GCA | CTT | CCC | CCT | 495 |
| CAG | CCC | CTG | TGG | TCT | GTT | CCT | CAG | CCC | AAA | GTC | CTG | CCT | ATC | CCC | 540 |
| CAG | CAA | GTG | GTG | CCC | TAC | CCT | CAG | AGA | GCT | GTG | CCT | GTT | CAA | GCC | 585 |
| CTT | CTG | CTC | AAC | CAA | GAA | CTT | CTA | CTT | AAC | CCC | ACC | CAC | CAG | ATC | 630 |
| TAC | CCT | GTG | ACT | CAG | CCA | CTT | GCC | CCA | GTT | CAT | AAC | CCC | ATT | AGT | 675 |
| GTC | TAA | GAA | GAT | TTC | AAA | GTT | AAT | TTT | CCC | TCC | TTA | TTT | TTG | AAT | 720 |
| TGA | CTG | AGA | CTG | GAA | ATA | TGA | TGC | CTT | TTC | CGT | CTT | TGT | ATC | ACG | 765 |
| TTA | CCC | CAA | ATT | AAG | TAT | GTT | TGA | ATG | AGT | TTA | TAT | GGA | AAA | AAT | 810 |
| GAA | CTT | TGT | CCC | TTT | ATT | TAT | TTT | ATA | TAT | TAT | GTC | ATT | CAT | TTA | 855 |
| ATT | TGA | AAT | TTG | ACT | CAT | GAA | CTA | TTT | ACA | TTT | TCC | AAA | TCT | TAA | 900 |
| TTC | AAC | TAG | TAC | CAC | AGA | AGT | TCA | ATA | CTC | ATT | TGG | AAA | TGC | TAC | 945 |
| AAA | CAT | ATC | AAA | CAT | ATG | TAT | ACA | AAT | TGT | TTC | TGG | AAT | TGT | GCT | 990 |
| TAT | TTT | TAT | TTC | TTT | AAG | AAT | CTA | TTT | CCT | TTC | CAG | TCA | TTT | CAA | 1035 |
| TAA | ATT | ATT | CTT | AAG | CAT | AAA | AAA | AAA | AAA | | | | | | 1065 |

(2) INFORMATION FOR SEQ ID NO: 2:

(i) SEQUENCE CHARACTERISTICS:

(A) LENGTH:105 base pairs
(B) TYPE:Nucleic acid
(C) STRANDEDNESS: Single
(D) TOPOLOGY: Unknown (ii) MOLECULE TYPE: Synthetic oligonucleotide.
(A) DESCRIPTION:

(iii) HYPOTHETICAL:

(iv) ANTI-SENSE:

(v) FRAGMENT TYPE:

(vi) ORIGINAL SOURCE: Synthetic Oligonucleotide Sequence
(A) ORGANISM:
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(vii) IMMEDIATE SOURCE:
(A) LIBRARY:
(B) CLONE:

(viii) POSITION IN GENOME:
(A) CHROMOSOME/SEGMENT:
(B) MAP POSITION:
(C) UNITS:

(ix) FEATURE:
(A) NAME/KEY:
(B) LOCATION:
(C) IDENTIFICATION METHOD: DNA sequencing and restriction analysis
(D) OTHER INFORMATION: The synthetic oligonucleotide assures adaptation of translation sequence to E. coli codon usage.

(x) PUBLICATION INFORMATION:
(A) AUTHORS: L. Hansson et al
(B) TITLE: Expression of Human Milk β-casein in Escherichia coli: Comparison of Recombinant Protein with Native Isoforms.
(C) JOURNAL:Protein Expression and Purification
(D) VOLUME:4
(E) ISSUE:
(F) PAGES:373–381
(G) DATE:1993
(H) DOCUMENT NUMBER:
(I) FILING DATE:
(J) PUBLICATION DATE:
(K) RELEVANT RESIDUES:

(xi) SEQUENCE DESCRIPTION: SEQ ID NO: 2:

| CTG | CAG | AAT | TCA | TAT | GCG | TGA | AAC | CAT | CGA | ATC | CCT | GAG | CTC | GAG | 45 |
| CGA | AGA | ATC | GAT | CAC | CGA | ATA | CAA | AAA | AGT | TGA | AAA | AGT | TAA | ACA | 90 |
| CGA | GGA | CCA | GGA | TCC | | | | | | | | | | | 105 |

(2) INFORMATION FOR SEQ ID NO: 3:

(i) SEQUENCE CHARACTERISTICS:
(A) LENGTH:71 base pairs
(B) TYPE:Nucleic acid
(C) STRANDEDNESS: Single
(D) TOPOLOGY: Unknown (ii) MOLECULE TYPE: Synthetic oligonucleotide.
(A) DESCRIPTION:

(iii) HYPOTHETICAL:

(iv) ANTI-SENSE:

( v ) FRAGMENT TYPE:

( v i ) ORIGINAL SOURCE: Synthetic Oligonucleotide Sequence
                        ( A ) ORGANISM:
                        ( B ) STRAIN:
                        ( C ) INDIVIDUAL ISOLATE:
                        ( D ) DEVELOPMENTAL STAGE:
                        ( E ) HAPLOTYPE:
                        ( F ) TISSUE TYPE:
                        ( G ) CELL TYPE:
                        ( H ) CELL LINE:
                        ( I ) ORGANELLE:

( v i i ) IMMEDIATE SOURCE:
                        ( A ) LIBRARY:
                        ( B ) CLONE:

( v i i i ) POSITION IN GENOME:
                        ( A ) CHROMOSOME/SEGMENT:
                        ( B ) MAP POSITION:
                        ( C ) UNITS:

( i x ) FEATURE:
                        ( A ) NAME/KEY:
                        ( B ) LOCATION:
                        ( C ) IDENTIFICATION METHOD: DNA sequencing and restriction
                                analysis
                        ( D ) OTHER INFORMATION: The synthetic oligonucleotide encodes
                                the carboxy- terminal end and translation stop.

( x ) PUBLICATION INFORMATION:
                        ( A ) AUTHORS: L. Hansson et al
                        ( B ) TITLE: Expression of Human Milk β-casein in Escherichia
                                coli: Comparison of Recombinant Protein with Native
                                Isoforms.
                        ( C ) JOURNAL:Protein Expression and Purification
                        ( D ) VOLUME:4
                        ( E ) ISSUE:
                        ( F ) PAGES:373–381
                        ( G ) DATE:1993
                        ( H ) DOCUMENT NUMBER:
                        ( I ) FILING DATE:
                        ( J ) PUBLICATION DATE:
                        ( K ) RELEVANT RESIDUES:

( x i ) SEQUENCE DESCRIPTION: SEQ ID NO: 3:

AGA  TCT  ACC  CTG  TGA  CTC  AGC  CAC  TTG  CCC  CAG  TTC  ATA  ACC  CCA                45

TTA  GTG  TCT  AAT  AAG  GAT  CCG  AAT  TC                                                71

( 2 ) INFORMATION FOR SEQ ID NO: 4:

( i ) SEQUENCE CHARACTERISTICS:
                ( A ) LENGTH:68 base pairs
                ( B ) TYPE:Nucleic acid
                ( C ) STRANDEDNESS: Single
                ( D ) TOPOLOGY: Unknown ( i i ) MOLECULE TYPE: Synthetic oligonucleotide.
                ( A ) DESCRIPTION:

( i i i ) HYPOTHETICAL:

( i v ) ANTI-SENSE:

( v ) FRAGMENT TYPE:

( v i ) ORIGINAL SOURCE: Synthetic Oligonucleotide Sequence
                ( A ) ORGANISM:
                ( B ) STRAIN:
                ( C ) INDIVIDUAL ISOLATE:
                ( D ) DEVELOPMENTAL STAGE:
                ( E ) HAPLOTYPE:
                ( F ) TISSUE TYPE:
                ( G ) CELL TYPE:
                ( H ) CELL LINE:
                ( I ) ORGANELLE:

```
      ( v i i ) IMMEDIATE SOURCE:
               ( A ) LIBRARY:
               ( B ) CLONE:

( v i i i ) POSITION IN GENOME:
               ( A ) CHROMOSOME/SEGMENT:
               ( B ) MAP POSITION:
               ( C ) UNITS:

( i x ) FEATURE:
               ( A ) NAME/KEY:
               ( B ) LOCATION:
               ( C ) IDENTIFICATION METHOD: DNA sequencing and restriction
                     analysis
               ( D ) OTHER INFORMATION: Modified enterotoxin STII signal
                     sequence.

( x ) PUBLICATION INFORMATION:
               ( A ) AUTHORS: L. Hansson et al
               ( B ) TITLE: Expression of Human Milk β-casein in Escherichia
                     coli: Comparison of Recombinant Protein with Native
                     Isoforms.
               ( C ) JOURNAL:Protein Expression and Purification
               ( D ) VOLUME:4
               ( E ) ISSUE:
               ( F ) PAGES:373-381
               ( G ) DATE:1993
               ( H ) DOCUMENT NUMBER:
               ( I ) FILING DATE:
               ( J ) PUBLICATION DATE:
               ( K ) RELEVANT RESIDUES:

( x i ) SEQUENCE DESCRIPTION: SEQ ID NO: 4:
```

CAT GAA AAA GAA TAT CGC ATT TCT TCT TGC ATC GAT GTT CGT TTT        45

TTC TAT TGC TAC AAA TGC ATA TG                                    68

```
( 2 ) INFORMATION FOR SEQ ID NO: 5:

( i ) SEQUENCE CHARACTERISTICS:
               ( A ) LENGTH:37 base pairs
               ( B ) TYPE:Nucleic acid
               ( C ) STRANDEDNESS: Single
               ( D ) TOPOLOGY: Unknown ( i i ) MOLECULE TYPE: Synthetic oligonucleotide.
               ( A ) DESCRIPTION:

( i i i ) HYPOTHETICAL:

( i v ) ANTI-SENSE:

( v ) FRAGMENT TYPE:

( v i ) ORIGINAL SOURCE: Synthetic Oligonucleotide Sequence
               ( A ) ORGANISM:
               ( B ) STRAIN:
               ( C ) INDIVIDUAL ISOLATE:
               ( D ) DEVELOPMENTAL STAGE:
               ( E ) HAPLOTYPE:
               ( F ) TISSUE TYPE:
               ( G ) CELL TYPE:
               ( H ) CELL LINE:
               ( I ) ORGANELLE:

( v i i ) IMMEDIATE SOURCE:
               ( A ) LIBRARY:
               ( B ) CLONE:

( v i i i ) POSITION IN GENOME:
               ( A ) CHROMOSOME/SEGMENT:
               ( B ) MAP POSITION:
               ( C ) UNITS:

( i x ) FEATURE:
               ( A ) NAME/KEY:
               ( B ) LOCATION:
```

(C) IDENTIFICATION METHOD: DNA sequencing and restriction
                analysis
            (D) OTHER INFORMATION:

( x ) PUBLICATION INFORMATION:
            (A) AUTHORS: L. Hansson et al
            (B) TITLE: Expression of Human Milk β-casein in Escherichia
                coli: Comparison of Recombinant Protein with Native
                Isoforms.
            (C) JOURNAL:Protein Expression and Purification
            (D) VOLUME:4
            (E) ISSUE:
            (F) PAGES:373-381
            (G) DATE:1993
            (H) DOCUMENT NUMBER:
            (I) FILING DATE:
            (J) PUBLICATION DATE:
            (K) RELEVANT RESIDUES:

( x i ) SEQUENCE DESCRIPTION: SEQ ID NO: 5:

CAT ATG CAC GTG AAA CCA TCG AAT CCC TGA GCT CGA G                                   3 7

We claim:

1. A liquid enteral nutritional product comprising at least one protein not contained in human milk but selected from the group consisting of bovine milk protein and vegetable protein in combination with at least one material selected from the group consisting of β-casein isolated from human milk, a recombinant form of the β-casein contained in human milk, and hydrolysates of both in a therapeutically effective amount that inhibits the infection of mammalian cells by respiratory syncytial virus.

2. A liquid enteral nutritional product according to claim 1 wherein the vegetable protein is soy protein.

3. A liquid enteral nutritional infant formula comprising at least one protein not contained in human milk but selected from the group consisting of bovine milk protein and vegetable protein in combination with at least one material selected from the group consisting of β-casein isolated from human milk, a recombinant form of the β-casein contained in human milk, and hydrolysates of both in a therapeutically effective amount that inhibits the infection of mammalian cells by respiratory syncytial virus, said infant formula containing no other proteins which are found in human milk.

4. A liquid enteral nutritional infant formula according to claim 3 wherein the vegetable protein is soy protein.

5. A nasally administrable formulation comprising at least one material selected from the group consisting of β-casein isolated from human milk, a recombinant form of the β-casein contained in human milk and hydrolysates of both in a therapeutically effective amount which inhibits the infection of mammalian cells by respiratory syncytial virus.

6. A throat spray formulation comprising at least one material selected from the, group consisting of β-casein isolated from human milk, a recombinant form of the β-casein contained in human milk and hydrolysates of both in a therapeutically effective amount which inhibits the infection of mammalian cells by respiratory syncytial virus.

* * * * *